United States Patent [19]

Long et al.

[11] Patent Number: 4,753,869

[45] Date of Patent: Jun. 28, 1988

[54] PHOTOGRAPHIC DEVELOPING AGENTS CONTAINING STABLE, SOLUBLE, PYRAZOLIDINONES

[75] Inventors: William E. Long, Wilmslow; Malcolm D. Tirel, Alderley Edge; Monica H. Gent, Macclesfield; Terence C. Webb, Wilmslow, all of England

[73] Assignee: Ciba-Geigy AG, Basel, Switzerland

[21] Appl. No.: 935,098

[22] Filed: Nov. 24, 1986

Related U.S. Application Data

[63] Continuation of Ser. No. 797,565, Nov. 13, 1985, abandoned.

[30] Foreign Application Priority Data

Nov. 30, 1984 [GB] United Kingdom ............... 8430328

[51] Int. Cl.$^4$ ........................... G03C 5/24; G03C 1/02
[52] U.S. Cl. ..................................... 430/465; 430/440; 430/481; 430/483; 548/363
[58] Field of Search ............... 430/465, 481, 483, 440; 260/239; 532/100

[56] References Cited

U.S. PATENT DOCUMENTS

| | | | |
|---|---|---|---|
| 2,444,803 | 7/1948 | Bean | 430/465 |
| 2,893,865 | 7/1959 | Welliver et al. | 430/465 |
| 3,038,801 | 6/1962 | Alletag et al. | 430/465 X |
| 3,241,967 | 3/1966 | DeMarle et al. | 430/481 X |
| 4,514,494 | 4/1985 | Lemahieu et al. | 430/380 X |

FOREIGN PATENT DOCUMENTS 943928 12/1963 United Kingdom .
1039875 8/1966 United Kingdom .

*Primary Examiner*—Mukund J. Shah
*Attorney, Agent, or Firm*—Wenderoth, Lind & Ponack

[57] ABSTRACT

Salts of 1-phenyl-3-pyrazolidinones with organic sulphonic acids, which are useful photographic silver halide developing agents.

5 Claims, No Drawings

PHOTOGRAPHIC DEVELOPING AGENTS CONTAINING STABLE, SOLUBLE, PYRAZOLIDINONES

This application is a continuation, of now abandoned application Ser. No. 797,565, filed Nov. 13, 1985.

This invention relates to new photographic developing agents and to compositions containing them.

It is well known that certain pyrazolidone compounds are often used in conjunction with hydroquinone in photographic super-additive developing compositions. An example of such a pyrazolidone compound which has found considerable commercial use is 1-phenyl-3-pyrazolidinone

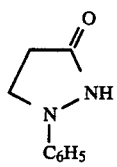
(I)

A substituted 1-phenyl-3-pyrazolidinone which is also used commercially is 4-hydroxymethyl-4-methyl-1-phenyl-3-pyrazolidinone

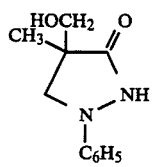
(II)

However one problem associated with the use of both these compounds is that they only dissolve slowly in water, and hence prolonged stirring or heating is necessary in order to make up solutions containing them. It is known according to British Patent Specification No. 943,928 that certain salts of pyrazolidones dissolve readily in water, for instance the compound of formula (III), the tosylate salt of 1-phenyl-3-pyrazolidinone:

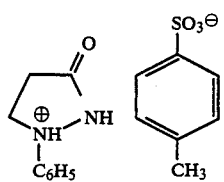
(III)

Unfortunately, although the salts described in said specification No. 943,928 are readily soluble in water, and may be formulated with other components to give rapidly dissolving powder developers, these formulations are not stable, due to interactions between the pyrazolidinone salt and other components present. Thus after storage and sometimes immediately on formulating the mixtures, these mixtures will not dissolve rapidly in water.

We have now prepared new salts of the compounds of formulae (I) and (II) to which this disadvantage does not apply. These new compounds dissolve readily in water even in the presence of other components, for example hydroquinone, sodium sulphite, and base, and give single bag powder developer compositions which are stable to storage.

According to the present invention there are provided four salts of the pyrazolidinones of the formulae (I) and (II) all of which act as photographic developing agents, all of which dissolve rapidly in water at room temperature and none of which react with hydroquinone in a powder composition which contains both hydroquinone and at least one of these salts, these four salts being:

the salt of 1-phenyl-3-pyrazolidinone

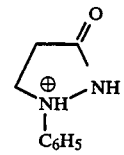

with either camphor-10-sulphoric acid of the formula:

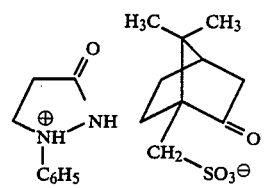
(IV)

or with 3-hydroxy propane sulphonic acid of the formula

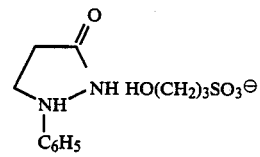
(V)

and the salt of 4-hydroxymethyl-4-methyl-1-phenyl-3-pyrazolidinone
with sulphosalicyclic acid of the formula

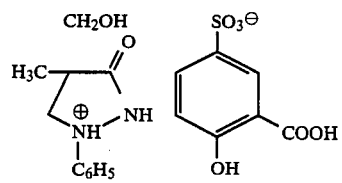
(VI)

or with 4-sulphophthalic acid of the formula

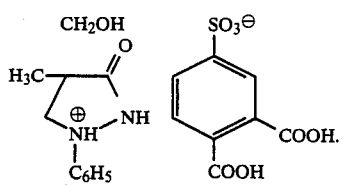
(VII)

The salts of the formulae (IV), (V), (VI) and (VII) are prepared by mixing the pyrazolidinone compound and the appropriate acid in a suitable solvent and then inducing crystallisation. A useful solvent is tetrahydrofuran.

A very large number of other salts of 1-phenyl-3-pyrazolidinone were tested, but the above four salts of the formulae (IV), (V), (VI) and (VII) were the only ones which were able to act as silver halide developing agents, which were readily water-soluble at room temperature and which did not react in a single powder composition with hydroquinone or other components.

Thus these salts are useful as the superadditive developing agent in single bag powder developer composition which comprise hydroquinone or substituted hydroquinone and optionally all the solid ingredients necessary to produce a silver halide developing solution.

Thus according to a second aspect of the present invention there is provided a single bag powder developer composition which comprises at least one pyrazolidinone salt of the formula (IV), (V), (VI) or (VII), hydroquinone or substituted hydroquinone, and optionally a base, a buffer system and a preservative. Optionally, there is also present an antifoggant, and a restrainer. The function of such additions is described in Photographic Processing Chemistry 2nd Edition by L. F. A. Mason, published by Focal Press 1975.

A suitable base is sodium carbonate. A suitable preservative which acts as an antioxidant is sodium sulphite. A suitable antifoggant is benzotriazole. A suitable buffer system is sodium tetraborate/boric acid. A suitable restrainer is potassium bromide.

The single powder developer compositions of the present invention dissolve rapidly at room temperature when added to water. They produce a developing solution as active as solutions which comprise compounds of formulae (I) and (II). No diminution of the developer activity is observed when the single bag powder developer compositions are stored for long periods of time.

The following examples will serve to illustrate the invention.

EXAMPLE 1

Synthesis of the Salt of the Formula (IV)

1-phenyl-3-pyrazolidinone (1.8 g) in tetrahydrofuran (THF) (35 ml) was mixed with 10-camphor-sulphonic acid (2.8 g) in THF (20 ml). The solvent was evaporated in vacuo to give an off-white solid Yield 3.7 g (80%), melting point 126°–129° C.

EXAMPLE 2

Synthesis of the Salt of the Formula (VI)

Compound II (1.0 g) in THF (35 ml) and ether (20 ml) was mixed with 5-sulphosalicyclic acid (1.27 g) in THF (15 ml) at room temperature. The solvent was evaporated to give a fawn solid Yield 1.81 g (80%), melting point 86°–90° C.

EXAMPLE 3

Synthesis of the Salt of the Formula (V)

3-Hydroxypropane sulphonic acid (5.19 g) in THF (75 ml) was added to 1-phenyl-3-pyrazolidinone (5 g) in THF (200 ml) at room temperature. The solution was evaporated to dryness and the product dissolved in hot ethanol (25 ml) and precipitated by adding ether (200 ml). A cream solid was produced, yield 7.25 g (78%), melting point 110°–120° C.

EXAMPLE 4

Synthesis of the Salt of the Formula (VII)

A 50% aqueous solution of 4-sulphophthalic acid (11.94 g) was added to compound II (5 g) in THF (150 ml) at room temperature. The solution was evaporated to dryness and the resulting cream powder was dried, yield 11 g, melting point 135°–142° C.

In all the Examples above n.m.r. spectroscopy was used to determine the 1:1 stoichiometry between the reagents and the protonated nature of the pyrazolidinone moiety.

EXAMPLE 5

Example of Use

A single bag developer powder was prepared containing the following ingredients:

| | |
|---|---|
| Hydroquinone | 1.5 g |
| Boric Acid | 0.8 g |
| Sodium Tetraborate | 2.0 g |
| Potassium Bromide | 0.3 g |
| Sodium Sulphite | 25.0 g–30.0 g (depending on salt used). |
| Pyrazolidinone Compound or Salt | 0.05–0.3 g, (depending on salt used). |

The pyrazolidinone type salts used were the previously known compound of formula (III) prepared according to said specification No. 943,928, and the salts of the formulae (IV), (V), (VI) and (VII) of the present invention.

The tests were carried out by mixing the above quantities of ingredients in a paper/foil laminate bag and heat-sealing and then by storage at 40° C. and 60%· relative humidity.

Solubility tests were carried out by measuring the time taken for the contents of the bags to dissolve in 280 ml of water at 20° C. with gentle stirring. The results are given in the table below

TABLE

| Time of Storage | (I) | (III) | (IV) | (V) | (VI) | (VII) |
|---|---|---|---|---|---|---|
| 0 Months | does not dissolve | 2 min | 2 min | 2 min | 2 min | 2 min |
| 1 Month | does not dissolve | does not dissolve completely | 2 min | 2 min | 2 min | 2 min |
| 2 Months | does not dissolve | does not dissolve completely | 2 min | 2 min | 2 min | 2 min |
| 3 Months | does not dissolve | does not dissolve completely | 2 min | 2 min | 2 min | 2 min |

Thus the previously known compounds do not give a stable single bag formulation, whereas the compounds of the present invention give stable soluble formulations.

The photographic activity of the liquid developer compositions which comprised salts of the formulae (IV), (V), (VI) and (VII) were compared with a freshly made up solution which contained 1-phenyl-3-pyrazolidinone of formula (I) which was dissolved up at 50° C. with constant stirring.

All these developing solutions from the freshly made up solutions to those made from powder compositions which had been stored for three months were very active silver halide developing solutions and as good as that made from the compound of formula (I). Thus all the compounds of the present invention are of great use as silver halide developing agents and when formulated as single powder developer compositions their activity is undiminished after at least three months storage.

We claim:

1. A single bag powder developer composition which comprises at least one pyrazolidinone salt of the formulas

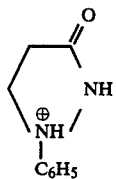 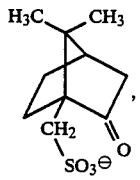

 HO(CH$_2$)$_3$SO$_3^\ominus$, or

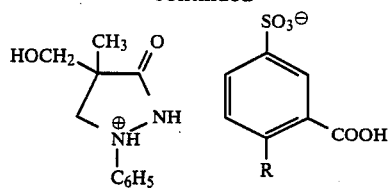

wherein R is —OH or —COOH, and hydroquinone or a substituted hydroquinone.

2. A single bag powder developer composition which comprises at least one pyrazolidinone salt according to claim 1 and hydroquinone or a substituted hydroquinone, a base, a buffer system and/or a preservative.

3. A single bag developer composition as claimed in claim 2 which also comprises a antifoggant and restrainer.

4. A single bag developer composition as claimed in claim 2 wherein the base is sodium carbonate.

5. A single bag developer composition as claimed in claim 2 wherein the buffer system is sodium tetraborate/boric acid.

* * * * *